United States Patent [19]

Jurecic

[11] 3,971,754
[45] July 27, 1976

[54] X-RAY OPAQUE, ENAMEL-MATCHING DENTAL FILLING COMPOSITION

[75] Inventor: Anton Jurecic, Springfield, Pa.

[73] Assignee: Pennwalt Corporation, Philadelphia, Pa.

[22] Filed: Dec. 10, 1973

[21] Appl. No.: 423,329

[52] U.S. Cl. .............................. 260/42.15; 32/15; 260/42; 260/42.52; 260/42.53; 260/998.11
[51] Int. Cl.² .................. A61K 5/06; C08K 3/40; C08K 9/06; C08L 33/12
[58] Field of Search ............ 260/40 R, 40 P, 998.11, 260/42.53, 42.52, 42.15, 42; 106/35; 32/15

[56] References Cited
UNITED STATES PATENTS

| | | | |
|---|---|---|---|
| 2,924,503 | 2/1960 | Reese | 18/54 |
| 3,037,960 | 6/1962 | Frazer | 260/45.4 |
| 3,066,112 | 11/1962 | Bowen | 260/37 EP |
| 3,194,784 | 7/1965 | Bowen | 260/47 EP |
| 3,227,665 | 1/1966 | Fourcade | 260/2.5 |
| 3,541,068 | 11/1970 | Taylor | 260/998.11 |
| 3,808,170 | 4/1974 | Rogers | 260/998.11 |
| 3,814,717 | 6/1974 | Wilson et al. | 106/35 |

FOREIGN PATENTS OR APPLICATIONS 626,249   1961   Belgium

*Primary Examiner*—Allan Lieberman

[57] ABSTRACT

An enamel-matching dental filling composition which is x-ray opaque and optically translucent utilizes a binder mixed with a ground glass filler containing compounds selected from the class consisting of oxides and carbonates of lanthanum, hafnium, strontium and tantalum.

7 Claims, No Drawings

X-RAY OPAQUE, ENAMEL-MATCHING DENTAL FILLING COMPOSITION

This invention relates to dental filling materials, and more particularly relates to compositions useful in dental restoration practice, such as fillings, cements, inlays and the like.

An important factor in dental restorations and surgical implants is that sufficient x-ray contrast be obtained whereby the position and boundary area of the implanted material is clearly delineated. Today, x-ray contrasts are the only non-destructive means to enable post operative examination such that recurrent caries, growth of neoplasms, and other tissue disorders may be detected without operative procedure.

While metallic dental restorations provide excellent opacity to x-ray radiation, they do have a shortcoming by virtue of their lack of aesthetic compatibility with human tooth enamel. In recent years, composite restorative materials have been found to be dependable replacements for amalgam restorations, their primary advantage residing in the ability to match them to the optical properties of tooth enamel and at the same time provide high mechanical strength. Many of these composites comprise a quartz filler and an organic type binder. The basic disadvantage of these prior composite restoratives is in their lack of x-ray absorption capacity thus yielding insufficient contrast between the placed restoration and the surrounding enamel and dentin.

Materials havng atoms of high atomic weight are known to provide a high x-ray absorption and hence yield a sufficient degree of x-ray contrast with biological tissue. However, there are physiological limitations to the use of heavy elements, especially since many of these are in themselves radioactive while non-radioactive isotopes of heavy atoms are usually toxic and unsafe to use in a human tissue environment. In addition, the presence of oxides of metals of high atomic number increases the refractive index of the glass formed therefrom (usually above 1.6) to the extent that they far exceed the refractive index of the dentin (approximately 1.56).

Up to now, the approach in preparing x-ray opaque composites has been to incorporate barium-containing glasses as the filler in a binder matrix. While the obtained x-ray opacity using barium glasses is generally satisfactory, physiological safety has never been fully established. See The Chemistry of Industrial Toxicology, 2nd ed., Hervey B. Elkins, John Wiley & Sons, 1959. It has also been determined that large quantities of $Ba^{+2}$ may be leached out when the set composite specimens are stored in distilled water at 37°C, barium glass being more easily hydrated than glasses containing less electro positive ions according to The Constitution of Glasses, W. A. Weyl and E. C. Marboe, Interscience Publ., 1962. Another disadvantage of barium glasses is that they must be fused at temperatures above 1350°C which requires special furnaces and safety precautions.

It is therefore an object of this invention to provide an x-ray opaque dental filling material having low toxicity, high mechanical strength, an optical translucency matching tooth enamel and chemical compatibility with the organic matrix in which it is incorporated.

Another object of this invention is to provide an x-ray opaque dental filler material resistant to attack by oral fluids which may penetrate into the restoration.

Still another object of this invention is to provide an x-ray opaque filler which will interact with organic binder matrices to form a strong interfacial bond.

Yet another object of this invention is to provide an x-ray opaque filler which will exhibit a refractive index in the range between 1.45 and 1.60, preferably 1.52 to 1.58 so that the set filling has partial translucency matching that of enamel and which will retain such matching translucency characteristics for the duration of the restoration.

The filler compositions of the instant invention include non-toxic, x-ray absorbing atoms, primarily lanthanum, strontium, and tantalum, and marginally hafnium, in the form of oxides or carbonates. The foregoing materials are embodied in a concentration in the range of about 5 to 60 percent, and preferably between 25 and 40 percent of the total fused glass composition which is then incorporated into the restorative matrix. The glass network into which the x-ray opaqueing materials are embedded is formed from 25 to 50 weight percent $SiO_2$ and preferably 30 to 40 percent, thus assuring that the continuity in —Si—O—Si— linkage is preserved to form a random grid structure in which highly electropositive metals, such as sodium, calcium and strontium are synergistically accommodated. $Al_2O_3$ is added as a glass network reinforcing oxide in the amounts between 5 and 30 percent, preferably between 10 and 20 percent. Boric acid performs a similar function as $Al_2O_3$ but in addition to the strength contribution it also helps to lower the fusion temperature by virtue of its lower melting point and sintering interaction with other components in the glass forming mixture. The amount of boric acid can be as high as 25 percent, the preferred quantity is 5 to 15 percent. X-ray opaque oxides, carbonates or fluorides embodied in this patent are represented by lanthanum oxide ($La_2O_3$) lanthanum carbonate ($La_2(CO_3)_3$) tantalum pentoxide, ($Ta_2O_5$) tantalum fluoride ($TaF_5$), strontium oxide (SrO), strontium carbonate ($SrCO_3$) and strontium fluoride ($SrF_2$). In addition to the oxides described above also needed in formation of glass are fluxes that function to bring the fusion temperature below 1350°C, the upper temperature limit of conventional industrial furnaces. As fluxing agents are added calcium fluoride ($CaF_2$) and sodium alumino fluoride ($Na_3AlF_6$) in the amounts up to 30 percent, preferably between 10 and 20 percent. The preferred amount depends on proper balancing between conflicting requirements of low fusion temperature, nucleation of fluoride salts, such as sodium fluoride in the melt and hydrolytic stability of fused and ground glass filler particles.

The optimum amount of x-ray opaque oxide or carbonate is determined empirically by combining glasses containing above oxides in varying proportions with finely ground quartz to which 1% benzoyl peroxide is added to catalyze the reaction with polyester binder that contains 1.5% of an aromatic amine, such as N, N-dimethyl-p-toluidine. After mixing for 30 seconds the composite material is placed into a plastic mold 5mm in diameter and 2mm long. The material is cured at 30°C for 60 minutes. X-ray absorption capacity of the cured specimen is determined by placing it in front of a dental x-ray unit at a distance of 20cm from the end of radiation tube and passing through it x-rays generated by electric current of 10 milliamps and 65 Kilovolts for ½ seconds using Kodak's ultraspeed pericapical x-ray film as a radiation intensity recording device. It has been found that the filler portion must contain at least 30% of x-ray opaque glass, the rest being quartz, to have sufficient x-ray opacity enabling dental practitioners to distinguish the x-ray opaque restoration from the adjacent tooth structure. There is no upper limit to the quantity of x-ray opaque glass being incorporated into the restorative composite, the higher the amount the more intense being absorption of x-rays placed after mixing for 30 seconds.

Other objects of the present invention are to provide an improved composition of the character described which is easily and economically produced, sturdy in construction, and highly efficient and effective in use.

The instant invention is illustrated by way of the following examples:

EXAMPLE 1

630 grams $SiO_2$ (quartz), 270 grams $Al_2O_3$, 720 grams $SrCO_3$, and 180 grams $Na_3AlF_6$ are intimately mixed in a ball mill. The mixture is placed in a ceramic crucible and fired in an electric furnace to a maximum temperature of 1350°C. The clear glassy melt is quenched by pouring into water, dried at 150°C., and ground in a ball mill until the average particle size is below 30 microns. The glass is then silane coated to make it compatible with the binder resin in the dental paste composition by placing the ground glass in a volatile solvent, such as methylene chloride or Isotron 113 ($CCl_2FCClF_2$ made by Pennwalt Corporation, of Philadelphia, Pennsylvania), and adding vinyl silane thereto plus trace amounts of an inorganic acid such as hydrochloric. The slurry is mixed thoroughly and evaporated at about 80°C. until the solvent is entirely removed leaving a silane coating on the glass particles. The glass has an index of refraction of 1.543 as determined by using a standard Becke line procedure, as described in Microscopy for Chemists, Harold F. Schaeffer, Dover Publications, 1966.

A dental paste is prepared using a binder made by reacting 0.5 mole of bisphenol A with 1 mole of glycidyl methacrylate in the presence of a small amount of a basic catalyst such as 0.2 parts N, N-dimethyl-p-toluidine. The synthesized binder is diluted with ethyleneglycol dimethyacrylate by blending 30 parts of the dimethacrylate with 70 parts of binder. The viscosity of the diluted polyester is 1700 centipoise as determined by using a Brookfield viscometer. Dental composite paste compositions are prepared by mixing 80 parts by weight of silane treated strontium glass particles with 20 parts of the foregoing binder diluted with ethyleneglycol dimethacrylate and stabilized with 250 parts per million of a polymerization inhibitor, such as monomethylether of hydroquinone. To 50 parts of such a paste is added 0.15 part polymerization catalyst such as benzoyl peroxide. To the second half of the paste is admixed 0.1 part of a polymerization co-catalyst such as N, N-dimethyl-p-toluidine. A dental filling is prepared by mixing for 30 seconds equal portions of a foregoing two pastes, usually 0.5 gram of each, on a glass slab using a plastic spatula. Such a mixed composite filling can then be immediately placed into the prepared dental cavity using a plastic spatula. It hardens to a stiff mass in 2 minutes and reaches within 10 minutes 90% of the final strength at the temperature of oral environment, 37°C.

Alternately a dental restorative filling can be made by using the foregoing glass filler containing 0.5% benzoyl peroxide and binder by mixing 1.5 grams of the above glass with 0.25 gram binder containing 1.5% aromatic tertiary amine such as N, N-dimethyl-p-toluidine on a glass slab or polyethylene coated paper using a plastic spatula. Dental restorative composites made by mixing the above glass and binder have higher mechanical properties than composites made by mixing two paste compositions.

In still another variation in the end use dispensation procedure, the above powder is placed into the chamber of a dental capsule, while the binder is filled into the retainer portion of capsule. Before use the binder is forced into the capsule chamber by either pressing or twisting the head of capsule, depending on the specific design. The capsule is placed into the clip of a dental amalgamator and mechanically mixed for 10 to 15 seconds, depending on the length of throw and the revolutions per minute of a particular instrument.

The mechanical strength of the dental restorative composite is determined by mixing together two pastes containing the glass of this invention, or the glass powder and liquid as described above, placing the mixed material into cylindrical molds, 6.0mm in diameter and 12.0mm long, curing the composite material at 37°C for 60 minutes, taking the cured specimens out of molds, storing them in distilled water at 37°C. for 24 hours and determining the compressive and diametral tensile strength in an Instron operating at a crosshead speed of 0.02 inch per minute.

The resulting restorative material is opaque to x-rays. The average compressive strength of the paste specimens is 42,000 psi and that of the powder-liquid composition is 45,000 psi.

EXAMPLE 2

In a ball mill is blended 800 grams $SiO_2$, 200 grams $Al_2O_3$, 100 grams $H_3BO_3$, 600 grams $La_2(CO_3)_3$, 100 grams $SrF_2$ and 200 grams $Na_3AlF_6$. The mixture was placed in a crucible and heated in an electric furnace to 1350°C. The resulting glass melt is quenched in water, dried, ground and used as filler in dental restorative compositions according to the description in Example 1. The specimens are partially transparent and have a refractive index of 1.533. All specimens are x-ray opaque.

EXAMPLE 3 800 Grams $SiO_2$, 500 grams $Al_2O_3$, 200 grams $Ta_2O_5$, 200 grams $CaF_2$ and 300 grams $Na_3AlF_6$ are mixed as in the examples above. The mixture was placed in a crucible and fired in an electric furnace at 1350°C. The clear fused glass had refractive index 1.525 and exhibits opacity to x-rays. It has a 24 hour compressive strength of 33,000 psi.

EXAMPLE 4

In a ball mill is blended 700 grams $SiO_2$, 400 grams $Al_2O_3$, 200 grams $H_2BO_3$, 100 grams $Ta_2O_5$, 400 grams $SrCO_3$, 100 grams $SrF_2$, and 100 grams $Na_3AlF_6$. The mixture is placed in a ceramic crucible and heated to 1350°C. The clear glass is x-ray opaque, has C.70 optical translucency of 0.52, and compressive strength of 36,000 psi.

EXAMPLE 5

A charge of 800 grams $SiO_2$, 400 grams $Al_2O_3$, 200 grams $H_3BO_3$, 400 grams of $SrCO_3$, and 200 grams $SrF_2$ is melted at 1350°C., treated like the glass in Example 1 and tested as glasses in previous examples. Refraction index of this glass is 1.55 and compressive strength is 37,000 psi.

EXAMPLE 6

A hafnium glass is prepared in accordance with the procedure of Example 1 by blending 400 grams $SiO_2$, 100 grams $Al_2O_3$, 50 grams $H_3BO_3$, 50 grams $SrF_2$, 100 grams $Na_3AlF_6$ and 300 grams $H_fO_2$. The hafnium glass while x-ray opaque, is also somewhat optically opaque, having an optical translucency at C.70 of 0.74. The refractive index is also high borderline, about 1 · 6+.

Toxicity tests on the foregoing materials were performed in accordance with "Recommended Standard Practices for Biological Evaluation of Dental Materials", JADA, 84, 382 (1972).

Samples were administered in cottonseed oil orally at a dose of 1.0 gm/kg to 10 sprague-Dowley male rats and the animals observed daily for two weeks. Acute Systemic Toxicity was considered non-toxic since no deaths or untoward effects was observed in any of the rats.

Mucus membrane irritation was determined by preparing a soft mass of the parts and inserting a sample into the cheek pouch of a Golden Syrian hamster (100–125 grams). In the other pouch was inserted a negative polyethylene control. After 20 minutes the pouches were examined for gross pathology. No gross irritation or pathology was observed as compared to polyethylene.

Implantation tests were conducted by mixing the base materials as described in the Examples and allowing the catalyzed materials to harden in thin rods. The rods were then implanted into six sites in the paraherteural muscles of a rabbit. After one week the rabbits were sacrificed and the sites of the implants examined for gross inflammatory response. Tissue immediate the implants were excised and examined histopathologically. None of the materials showed any gross tissue response and all materials were considered non-toxic.

Although this invention has been described in considerable detail, such description is intended as being illustrative rather than limiting, since the invention may be variously embodied, and the scope of the invention is to be determined as claimed.

What is claimed is:

1. In a dental filling composition having a binder resin made of condensation products from the reaction of bisphenol A with glycidyl methacrylate, said binder being in the presence of a diluent and intermixed with a fused glass filler in finely divided particulate form containing 25 to 50 weight percent $SiO_2$ and a sufficient amount of fluxing agent to bring the fusion temperature below 1350°C, the improvement comprising said glass filler including, at the time of fusing thereof, about 5 to 60 percent by weight of a compound selected from the class consisting of oxides and carbonates of lanthanum, hafnium, strontium and tantalum, to provide a non-toxic, x-ray opaque and optically translucent restorative matrix resistant to oral fluids.

2. The composition of claim 1 wherein said glass filler includes, at the time of fusion, a sufficient amount of fluxing agent selected from the class consisting of $Na_3AlF_6$ and $CaF_2$ to lower the fusion temperature of the glass to below 1350°C.

3. The composition of claim 2 wherein said glass filler contains between about 25 and 40 percent of the x-ray opaquing compounds and about 25 to 50 percent $SiO_2$.

4. The composition of claim 3 wherein the glass filler at the time of fusing includes between about 5 to 30 percent of a glass network reinforcing agent selected from the class consisting of $Al_2O_3$ and $H_3BO_3$.

5. The composition of claim 4 wherein the glass filler when intermixed with the binder resin has an average particle size of less than 30 microns.

6. The composition of claim 1 wherein the glass particles are coated with vinyl silane prior to intermixing with the binder resin.

7. The composition of claim 6 wherein about 4 to 6 parts of glass filler is intermixed with one part of binder containing a polymerization catalyst.

\* \* \* \* \*